United States Patent
Junger et al.

(10) Patent No.: US 11,666,482 B2
(45) Date of Patent: Jun. 6, 2023

(54) PERSONALIZATION OF EXCIMER LASER FIBERS

(71) Applicant: ELIOS VISION, INC., Los Angeles, CA (US)

(72) Inventors: Johannes Junger, Gilching (DE); Markus Enders, Munich (DE)

(73) Assignee: Elios Vision, Inc., Los Angeles, CA (US)

(*) Notice: Subject to any disclaimer, the term of this patent is extended or adjusted under 35 U.S.C. 154(b) by 0 days.

(21) Appl. No.: 17/644,930

(22) Filed: Dec. 17, 2021

(65) Prior Publication Data

US 2022/0183887 A1  Jun. 16, 2022

Related U.S. Application Data

(63) Continuation of application No. 16/389,425, filed on Apr. 19, 2019, now Pat. No. 11,234,866.

(51) Int. Cl.
*A61F 9/008* (2006.01)

(52) U.S. Cl.
CPC ... *A61F 9/00836* (2013.01); *A61F 2009/00865* (2013.01); *A61F 2009/00891* (2013.01)

(58) Field of Classification Search
CPC ........ A61F 9/00836; A61F 2009/00865; A61F 2009/00891; A61F 9/008; A61F 9/0084; A61F 2009/00855; H01S 3/10069; H01S 3/1305; H01S 3/2253; H01S 3/225; H01S 3/0014; H01S 3/10038
See application file for complete search history.

(56) References Cited

U.S. PATENT DOCUMENTS

| | | | |
|---|---|---|---|
| 4,607,622 A | 8/1986 | Fritch et al. |
| 4,846,172 A | 7/1989 | Berlin |
| 4,862,888 A | 9/1989 | Yessik |
| 5,281,241 A | 1/1994 | Patel |
| 5,323,766 A | 6/1994 | Uram |
| 5,738,677 A | 4/1998 | Colvard et al. |
| 5,755,716 A | 5/1998 | Garito et al. |
| 5,865,831 A | 2/1999 | Cozean et al. |
| 6,197,056 B1 | 3/2001 | Schachar |
| 6,283,974 B1 | 9/2001 | Alexander |
| 6,743,221 B1 | 6/2004 | Hobart et al. |
| 7,443,296 B2 | 10/2008 | Mezhinsky et al. |

(Continued)

FOREIGN PATENT DOCUMENTS

| | | |
|---|---|---|
| DE | 19920615 A1 | 12/2000 |
| DE | 10023176 A1 | 11/2001 |

(Continued)

OTHER PUBLICATIONS

Crandall, Alan, "Combining Cataract and Glaucoma Surgery", Review of Ophthalmology, 1-4, Jun. 13, 2008.

(Continued)

*Primary Examiner* — Ankit D Tejani
*Assistant Examiner* — Joshua Brendon Solomon
(74) *Attorney, Agent, or Firm* — Greenberg Traurig, LLP; David J. Dykeman; Roman Fayerberg

(57) ABSTRACT

The invention provides personalized laser probes for use in laser systems, wherein each laser probe includes one or more characteristics tailored to a given user to thereby improve performance of and outcome of a laser treatment procedure.

23 Claims, 7 Drawing Sheets

(56) References Cited

U.S. PATENT DOCUMENTS

| | | |
|---|---|---|
| 7,568,619 B2 | 8/2009 | Todd et al. |
| 7,801,271 B2 | 9/2010 | Gertner et al. |
| 9,489,785 B2 | 11/2016 | Klammer et al. |
| 9,642,746 B2 | 5/2017 | Berlin |
| 11,076,933 B2 | 8/2021 | Junger et al. |
| 11,076,992 B2 | 8/2021 | Junger et al. |
| 11,103,382 B2 | 8/2021 | Junger et al. |
| 11,234,866 B2 | 2/2022 | Junger et al. |
| 11,389,239 B2 | 7/2022 | Junger et al. |
| 11,464,677 B2 | 10/2022 | Junger et al. |
| 11,529,260 B2 | 12/2022 | Junger et al. |
| 2002/0013572 A1 | 1/2002 | Berlin |
| 2002/0183726 A1 | 12/2002 | Elbrecht et al. |
| 2004/0082939 A1 | 4/2004 | Berlin |
| 2004/0114879 A1 | 6/2004 | Hiereth et al. |
| 2004/0147985 A1 | 7/2004 | MacFarland et al. |
| 2005/0192480 A1 | 9/2005 | Toriya et al. |
| 2005/0283148 A1 | 12/2005 | Janssen et al. |
| 2006/0111699 A1 | 5/2006 | Neuberger |
| 2006/0244652 A1 | 11/2006 | Tethrake et al. |
| 2007/0027443 A1* | 2/2007 | Rose ............... A61B 18/22 |
| | | 433/29 |
| 2007/0122096 A1 | 5/2007 | Temelkuran et al. |
| 2007/0147752 A1 | 6/2007 | Weisberg et al. |
| 2007/0219601 A1 | 9/2007 | Neuberger |
| 2007/0265602 A1 | 11/2007 | Mordaunt et al. |
| 2008/0054073 A1 | 3/2008 | Charles |
| 2008/0082078 A1 | 4/2008 | Berlin |
| 2008/0097415 A1 | 4/2008 | Zimare et al. |
| 2008/0108981 A1 | 5/2008 | Telfair et al. |
| 2008/0108983 A1 | 5/2008 | Nadolski |
| 2008/0161781 A1 | 7/2008 | McArdle et al. |
| 2008/0269734 A1 | 10/2008 | Vila Echague et al. |
| 2009/0118715 A1 | 5/2009 | Mansour |
| 2009/0157064 A1 | 6/2009 | Hodel |
| 2010/0019125 A1 | 1/2010 | Stefani et al. |
| 2010/0068141 A1 | 3/2010 | Kaushal et al. |
| 2010/0324543 A1 | 12/2010 | Kurtz et al. |
| 2011/0295243 A1 | 12/2011 | Peyman |
| 2012/0275481 A1 | 11/2012 | Riggs |
| 2013/0041357 A1 | 2/2013 | Neuberger |
| 2013/0085484 A1 | 4/2013 | Van Valen et al. |
| 2014/0058367 A1 | 2/2014 | Dantus |
| 2014/0188096 A1 | 7/2014 | Chia et al. |
| 2014/0316388 A1 | 10/2014 | Hipsley |
| 2015/0051607 A1 | 2/2015 | Hajishah et al. |
| 2015/0148615 A1 | 5/2015 | Brennan et al. |
| 2015/0217133 A1 | 8/2015 | Angeley et al. |
| 2015/0297408 A1 | 10/2015 | Dolzan et al. |
| 2015/0305811 A1 | 10/2015 | Neuberger |
| 2015/0366706 A1 | 12/2015 | Belkin et al. |
| 2015/0374549 A1 | 12/2015 | Scott |
| 2017/0100041 A1 | 4/2017 | Kasamatsu et al. |
| 2017/0202708 A1 | 7/2017 | Berlin |
| 2017/0304001 A1 | 10/2017 | Searle et al. |
| 2018/0000337 A1 | 1/2018 | Chen et al. |
| 2018/0042772 A1 | 2/2018 | Mansour |
| 2018/0263647 A1 | 9/2018 | Aljuri et al. |
| 2018/0303667 A1 | 10/2018 | Peyman |
| 2018/0353328 A1 | 12/2018 | Bacher et al. |
| 2018/0360310 A1 | 12/2018 | Berlin |
| 2019/0105200 A1 | 4/2019 | Hipsley |
| 2019/0117459 A1 | 4/2019 | Berlin |
| 2019/0262071 A1 | 8/2019 | Thom |
| 2020/0078216 A1 | 3/2020 | Raksi |
| 2020/0078217 A1 | 3/2020 | Raksi |
| 2020/0330157 A1 | 10/2020 | Junger et al. |
| 2020/0330181 A1 | 10/2020 | Junger et al. |
| 2020/0330266 A1 | 10/2020 | Junger et al. |
| 2020/0330274 A1 | 10/2020 | Junger et al. |
| 2020/0330275 A1 | 10/2020 | Junger et al. |
| 2020/0330279 A1 | 10/2020 | Junger et al. |
| 2020/0330280 A1 | 10/2020 | Junger et al. |
| 2020/0330281 A1 | 10/2020 | Junger et al. |
| 2020/0390600 A1 | 12/2020 | Perera et al. |
| 2021/0259880 A1 | 8/2021 | Newton et al. |
| 2021/0298945 A1 | 9/2021 | Juhasz et al. |
| 2022/0022997 A1 | 1/2022 | Junger et al. |
| 2022/0023098 A1 | 1/2022 | Junger et al. |
| 2022/0031513 A1 | 2/2022 | Junger et al. |
| 2022/0151828 A1 | 5/2022 | Junger et al. |
| 2022/0183887 A1 | 6/2022 | Junger et al. |

FOREIGN PATENT DOCUMENTS

| | | |
|---|---|---|
| DE | 10138984 A1 | 3/2003 |
| EP | 1835862 B1 | 6/2011 |
| EP | 2120760 B1 | 9/2015 |
| WO | 2019060756 A1 | 3/2019 |
| WO | 2020215062 A1 | 10/2020 |
| WO | 2020215064 A1 | 10/2020 |
| WO | 2020215066 A1 | 10/2020 |
| WO | 2020215067 A1 | 10/2020 |
| WO | 2020215068 A1 | 10/2020 |
| WO | 2020215069 A1 | 10/2020 |
| WO | 2020215071 A1 | 10/2020 |
| WO | 2020215073 A1 | 10/2020 |

OTHER PUBLICATIONS

Grover, Davinder S. "When You Have Cataracts and Glaucoma", Glaucoma Research Foundation, Oct. 29, 2017.

Leung et al. "Anterior Chamber Angle Measurement with Anterior Segment Optical Coherence Tomography: A Comparison between Slit Lamp OCT and Visante OCT" IOVS, Aug. 2008, 3469-3474 (Year: 2008).

Taliaferro, Kevin et al. "Excimer Laser Trabeculostomy Normalizing IOP and Restoring Physiologic Outflow in Glaucoma." Glaucoma Today, 2009, pp. 45-47 (Year: 2009).

Toteberg-Harms, et al., "Cataract surgery combined with excimer laser trabeculotomy to lower intraocular pressure: effectiveness dependent on preoperative IOP." BMC ophthalmology, vol. 13, No. 1, p. 24 (2013).

Tsai, James C. "High Eye Pressure and Glaucoma", Glaucoma Research Foundation, Oct. 29, 2017.

International Search Report in International Application No. PCT/US2020/028974 dated Sep. 14, 2020.

Berlin et al., "Excimer Laser Trabeculostomy: An Effective Microinvasive Glaucoma Surgery Procedure for Open-Angle Glaucoma", published Dec. 19, 2013 Third Party Submission in Jan. 1, 2003.

Dietlein et al., "Erbium: YAG Laser Trabecular Ablation (LTA) in the Surgical Treatment of Glaucoma", Lasers in Surgery and Medicine, Jan. 6, 1999, vol. 23, pp. 104-110.

ExTra Operating Instructions, Manufacturer: Mlase AG, published prior to Jan. 1, 2018.

Francis et al., "Combined Cataract Extraction and Trabeculotomy by the Internal Approach for Coexisting Cataract and Open-Angle Glaucoma: Initial Results", Journal of Cataract & Refractive Surgery, Jul. 1, 2008, vol. 34, pp. 1096-1103.

Investigation Testing Authorization Application, TUI Laser AG, Published Jan. 1, 2016.

Wilmsmeyer et al., "Excimer Laser Trabeculotomy: A New, Minimally Invasive Procedure for Patients With Glaucoma", Graefe's Archive for Clinical and Experimental Ophthalmology, Oct. 19, 2005, vol. 244, pp. 670-676.

* cited by examiner

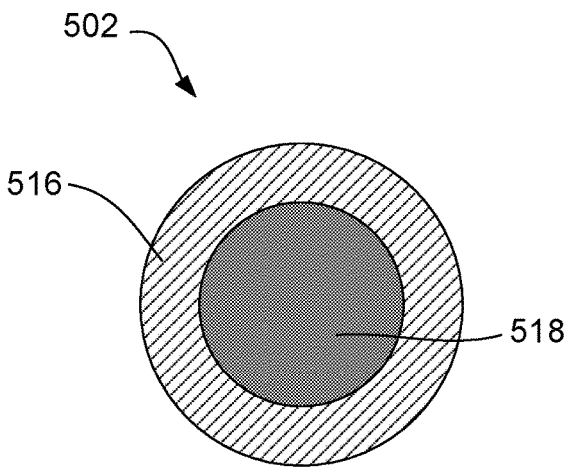
FIG. 7
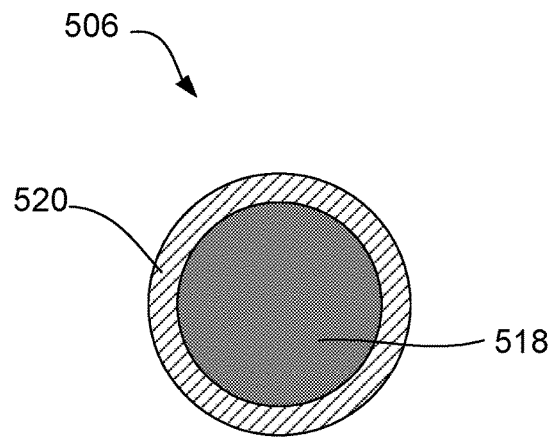
FIG. 8
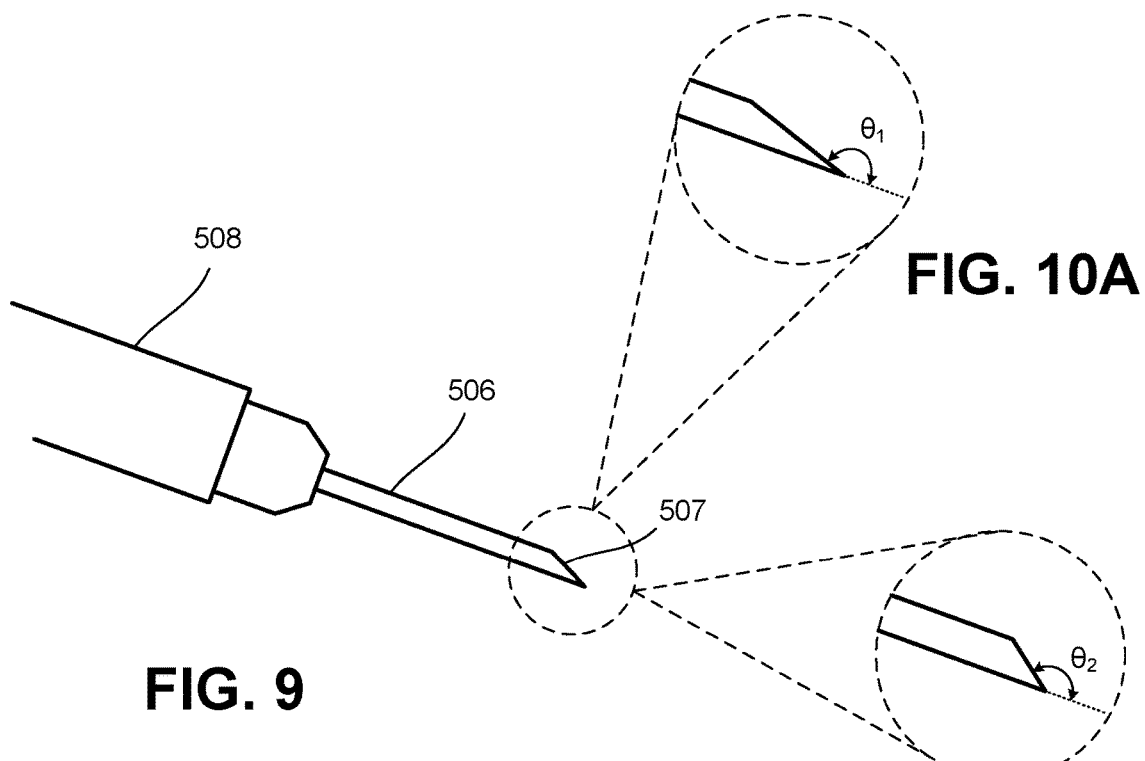
FIG. 9
FIG. 10A
FIG. 10B

PERSONALIZATION OF EXCIMER LASER FIBERS

RELATED APPLICATIONS

This application is a continuation patent application of U.S. application Ser. No. 16/389,425, filed Apr. 19, 2019, which is incorporated herein by reference in its entirety.

TECHNICAL FIELD

The disclosure relates to optical fibers for use in medical laser systems.

BACKGROUND

Glaucoma is a group of eye conditions which result in damage to the optic nerve and lead to vision loss. While glaucoma can occur at any age, it is more common in older adults and is one of the leading causes of blindness for people over the age of 60. A major risk factor in glaucoma is ocular hypertension, in which intraocular pressure is higher than normal. An elevated intraocular pressure can lead to atrophy of the optic nerve, subsequent visual field disturbances, and eventual blindness if left untreated.

Intraocular pressure is a function of the production of aqueous humor fluid by the ciliary processes of the eye and its drainage through a tissue called the trabecular meshwork. The trabecular meshwork is an area of tissue in the eye located around the base of the cornea and is responsible for draining the aqueous humor into a lymphatic-like vessel in the eye called Schlemm's canal, which subsequently delivers the drained aqueous humor into the bloodstream. Proper flow and drainage of the aqueous humor through the trabecular meshwork keeps the pressure inside the eye normally balanced. In open-angle glaucoma, the most common type of glaucoma, degeneration or obstruction of the trabecular meshwork can result in slowing or completely preventing the drainage of aqueous humor, causing a buildup of fluid, which increases the intraocular pressure. Under the strain of this pressure, the optic nerve fibers become damaged and may eventually die, resulting in permanent vision loss.

If treated early, it is possible to slow or stop the progression of glaucoma. Depending on the type of glaucoma, treatment options may include eye drops, oral medications, surgery, laser treatment, or a combination of any of these. For example, treatment of open-angle glaucoma may include surgical treatments, such as filtering surgery, in which an opening is created in the sclera of the eye and a portion of the trabecular meshwork is removed, and surgical implantation of stents or implants (i.e., drainage tubes), in which a small tube shunt is positioned within the eye to assist in fluid drainage. However, such treatments are highly invasive and may present many complications, including leaks, infections, hypotony (e.g., low eye pressure), and require post-operative, long-term monitoring to avoid late complications.

More recently, minimally invasive laser treatments have been used to treat glaucoma. In such treatments, the surgeon uses a laser to thermally modify and/or to puncture completely through various structures, including the trabecular meshwork and/or Schlemm's canal. For example, a laser trabeculostomy is a procedure in which a surgeon guides a working end of a laser fiber through a corneal incision of the eye and towards the trabecular meshwork and applies laser energy to destroy portions of the meshwork to create channels in the meshwork which allow aqueous humor to flow more freely into the Schlemm's canal. A great degree of precision is required during minimally invasive laser treatments. For example, a surgeon must be able to properly position the laser fiber at a correct position relative to the trabecular meshwork and Schlemm's canal to ensure that the resulting perforations, or channels, created by the laser are optimal. However, current laser fiber options are limited. Most laser fibers are similarly constructed and have similar features. As a result, surgeons have very few options when selecting a laser fiber of their choice. Rather, surgeons are forced to use laser fibers that lack certain qualities that a given surgeon requires when performing certain procedures, such as desired feel, feedback, and overall function of a laser fiber. As a result, the laser treatment may be inadequate, as the desired drainage may not be achieved, and thus patients may require additional post-operative procedures to lower the intraocular pressure. For example, with current laser fiber options, a surgeon may position the laser too close or too far from the trabecular meshwork and Schlemm's canal and/or position the laser at improper angles relative to the trabecular meshwork and Schlemm's canal, resulting in unintended collateral tissue damage or the creation of channels that inadequate and do not provide the desired drainage.

SUMMARY

The present invention provides personalized laser probes for use in laser systems. The laser probes are single-use, disposable probes configured for use with a laser unit. The laser unit includes a laser source for generating laser energy to be provided to a laser probe coupled thereto. Each laser probe is a handheld device, which includes a handheld body and an optical fiber, including a fiber optic core, extending therethrough. Upon coupling the laser probe to the laser unit, the fiber optic core is adapted to direct laser radiation from the laser source to delivery tip of the probe for transmitting laser energy to a desired treatment area. Each laser probe includes one or more characteristics tailored to a given user (e.g., a surgeon or other medical professional to perform a procedure involving laser treatment).

The specific characteristics of any given probe are based on individual preferences of a given user. The characteristics may generally relate to shape and/or dimensions of portions of the probe as well as physical qualities of portions of the probe. In some embodiments, the handheld body of a given probe may include specific dimensions, including width, length, and diameter, based on individual preferences of a surgeon to improve fit and feel. In some embodiments, the profile of the delivery tip of the fiber optic core may be shaped based on preferences of a surgeon, wherein the tip may be beveled at a desired angle to enable more precise control over the procedure. In some embodiments, the distal end of the laser probe may have a specific degree of flexibility or rigidity based on based on preferences of a surgeon, further providing improved feel and maneuverability over the procedure.

The personalization of laser probes provides surgeons with tailored fit, feel, and function. Surgeons are better equipped to successfully perform a given procedure that may otherwise prove difficult due to the lack of variation among laser fiber options. In particular, the laser probes and laser unit of the present invention are preferably used for permanent treatment of glaucoma using laser trabeculostomy. By providing personalized laser probes, a surgeon is more comfortable with the laser probe and able to perform the procedure with the required precision to ensure optimal laser treatment of the target area. In particular, by using a personalized laser probe, the surgeon is able to better position laser emission transverse to the Schlemm's canal, to create perforations, or channels, to improve fluid drainage, increase flow of aqueous humor, and reduce pressure in the eye. Arranging the laser probe at a position transverse to Schlemm's canal provides optimum results by providing a greater amount of surface area for photoablation by the laser, resulting in improved perforation and thus improved fluid drainage.

BRIEF DESCRIPTION OF THE DRAWINGS

FIG. 7 shows a cross-sectional view of the probe taken along line A-A of FIG. 6.

FIG. 8 shows a cross-sectional view of the probe taken along line B-B of FIG. 6.

FIG. 9 shows an enlarged view of a distal portion of a probe.

FIGS. 10A and 10B show enlarged views of delivery tips of a probe having different bevel angles.

DETAILED DESCRIPTION

The present invention provides personalized laser probes for use in laser systems. The laser probes are single-use, disposable probes configured for use with a laser unit. The laser unit includes a laser source for generating laser energy to be provided to a laser probe coupled thereto. Each laser probe is a handheld device, which includes a handheld body and an optical fiber, including a fiber optic core, extending therethrough. Upon coupling the laser probe to the laser unit, the fiber optic core is adapted to direct laser radiation from the laser source to delivery tip of the probe for transmitting laser energy to a desired treatment area.

Each laser probe includes one or more characteristics tailored to a given user (e.g., a surgeon or other medical professional to perform a procedure involving laser treatment). The personalization of laser probes provides surgeons with tailored fit, feel, and function. Surgeons are better equipped to successfully perform a given procedure that may otherwise prove difficult due to the lack of variation among laser fiber options. In particular, the laser probes and laser unit of the present invention are preferably used for permanent treatment of glaucoma using laser trabeculostomy. By providing personalized laser probes, a surgeon is more comfortable with the laser probe and able to perform the procedure with the required precision to ensure optimal laser treatment of the target area. In particular, by using a personalized laser probe, the surgeon is able to better position laser emission transverse to the Schlemm's canal, to create perforations, or channels, to improve fluid drainage, increase flow of aqueous humor and reduce pressure in the eye. Arranging the laser probe at a position transverse to Schlemm's canal provides optimum results by providing a greater amount of surface area for photoablation by the laser, resulting in improved perforation and thus improved fluid drainage.

The system of the present invention is particularly well suited for intraocular procedures in which laser treatment of target tissues is desired. In particular, the laser source and laser probes of the present invention are preferably used for treating glaucoma and useful in performing a laser trabeculostomy. However, it should be noted that the system consistent with the present disclosure can be used in any laser treatment of various conditions, including other eye conditions (i.e., diabetic eye diseases, such as proliferative diabetic retinopathy or macular oedema, cases of age-related macular degeneration, retinal tears, and retinopathy of prematurity, and laser-assisted in situ keratomileusis (LASIK) to correct refractive errors, such as short-sightedness (myopia) or astigmatism) as well as other conditions in general and other practice areas (non-ocular practice areas).

Figure 1:
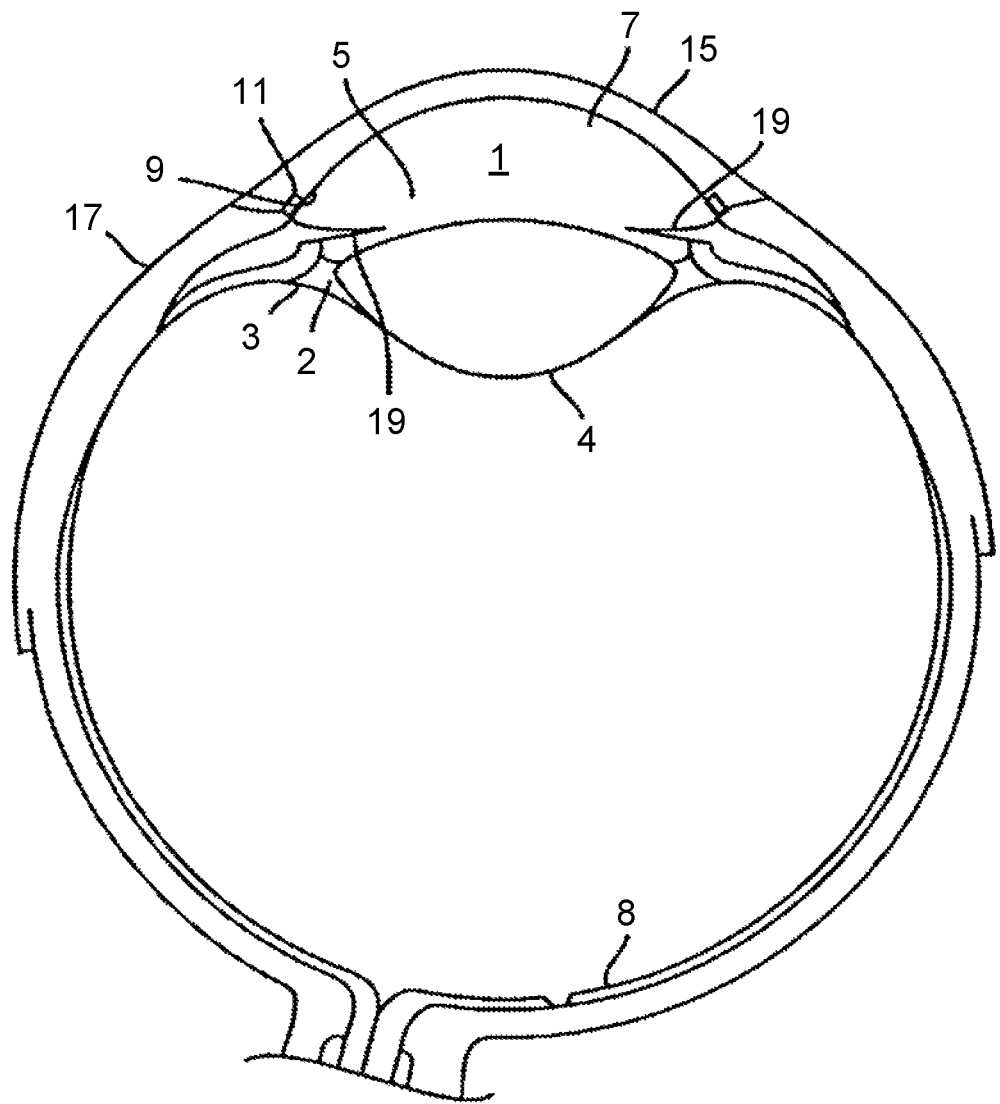
FIG. 1 is schematic sectional view of an eye illustrating the interior anatomical structure.

In order to fully appreciate the present invention, a brief overview of the anatomy of the eye is provided. FIG. 1 is schematic sectional view of an eye illustrating the interior anatomical structure. As shown, the outer layer of the eye includes a sclera 17 that serves as a supporting framework for the eye. The front of the sclera includes a cornea 15, a transparent tissue that enables light to enter the eye. An anterior chamber 7 is located between the cornea 15 and a crystalline lens 4. The anterior chamber 7 contains a constantly flowing clear fluid called aqueous humor 1. The crystalline lens 4 is connected to the eye by fiber zonules, which are connected to the ciliary body 3. In the anterior chamber 7, an iris 19 encircles the outer perimeter of the lens 4 and includes a pupil 5 at its center. The pupil 5 controls the amount of light passing through the lens 4. A posterior chamber 2 is located between the crystalline lens 4 and the retina 8.

Figure 2:
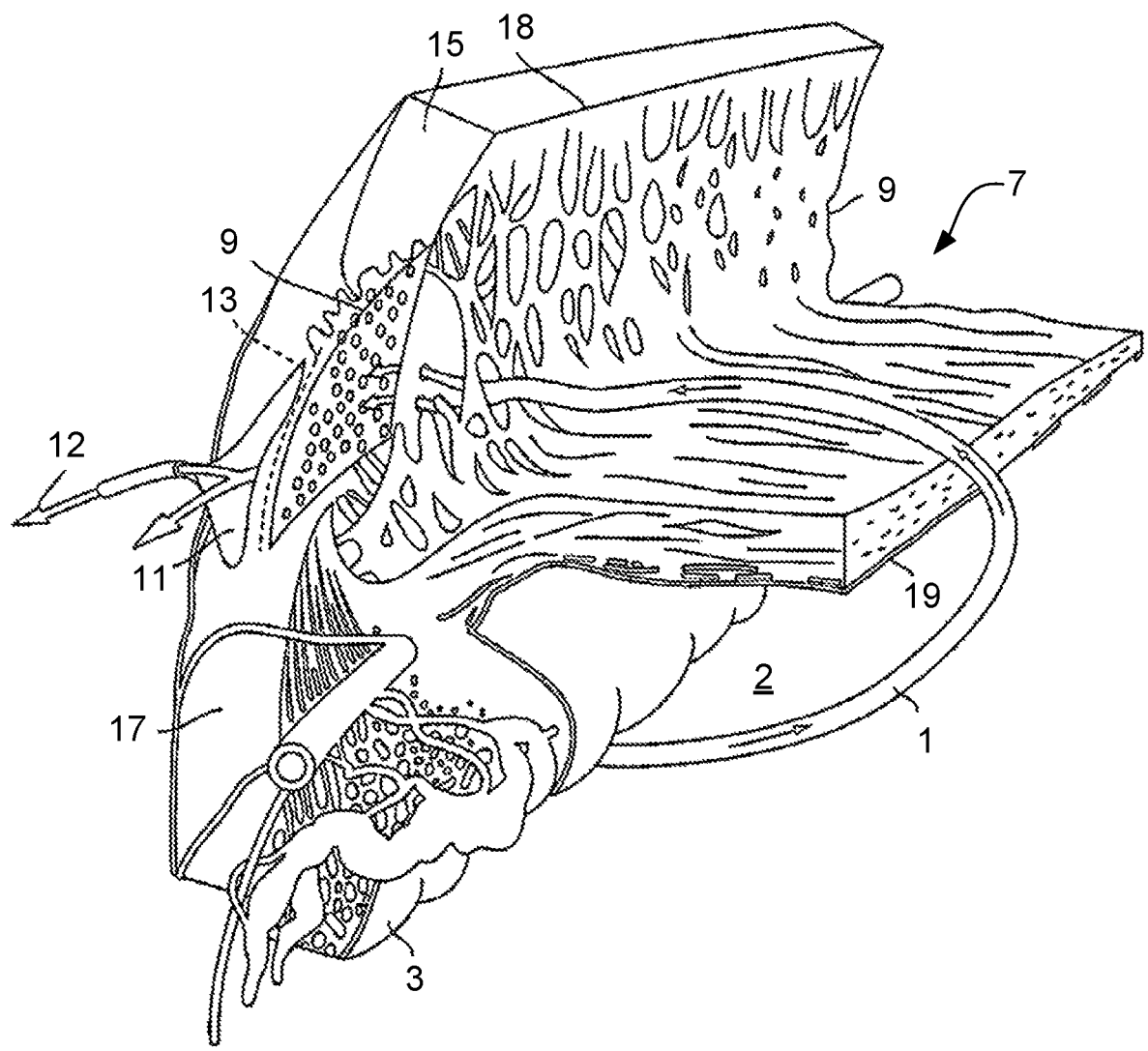
FIG. 2 is a perspective fragmentary view of the anatomy within the anterior chamber of an eye depicting the corneoscleral angle.

FIG. 2 is a perspective fragmentary view of the anatomy within the anterior chamber of an eye depicting the corneoscleral angle. As shown, the anatomy of the eye further includes a trabecular meshwork 9, which is a narrow band of spongy tissue that encircles the iris 19 within the eye. The trabecular meshwork has a variable shape and is microscopic in size. It is of a triangular cross-section and of varying thickness in the range of 100-200 microns. It is made up of different fibrous layers having micron-sized pores forming fluid pathways for the egress of aqueous humor. The trabecular meshwork 9 has been measured to about a thickness of about 100 microns at its anterior edge, Schwalbe's line 18, which is at the approximate juncture of the cornea 15 and sclera 17.

The trabecular meshwork widens to about 200 microns at its base where it and iris 19 attach to the scleral spur. The passageways through the pores in trabecular meshwork 9 lead through very thin, porous tissue called the juxtacanalicular trabecular meshwork 13 that in turn abuts the interior side of a structure called Schlemm's canal 11. Schlemm's canal 11 is filled with a mixture of aqueous humor and blood components and branches off into collector channels 12 which drain the aqueous humor into the venous system. Because aqueous humor is constantly produced by the eye, any obstruction in the trabecular meshwork, the juxtacanalicular trabecular meshwork or in Schlemm's canal prevents the aqueous humor from readily escaping from the anterior eye chamber which results in an elevation of intraocular pressure within the eye.

The eye has a drainage system for the draining aqueous humor 1 located in the corneoscleral angle. In general, the ciliary body 3 produces the aqueous humor 1. This aqueous humor flows from the posterior chamber 2 through the pupil 5 into the anterior chamber 7 to the trabecular meshwork 9 and into Schlemm's canal 11 to collector channels 12 to aqueous veins. The obstruction of the aqueous humor outflow which occurs in most open angle glaucoma (i.e., glaucoma characterized by gonioscopically readily visible trabecular meshwork) typically is localized to the region of the juxtacanalicular trabecular meshwork 13, which is located between the trabecular meshwork 9 and Schlemm's canal 11, more specifically, the inner wall of Schlemm's canal. It is desirable to correct this outflow obstruction by enhancing the eye's ability to use the inherent drainage system.

When an obstruction develops, for example, at the juxtacanalicular trabecular meshwork 13, intraocular pressure gradually increases over time, thereby leading to damage and atrophy of the optic nerve, subsequent visual field disturbances, and eventual blindness if left untreated. The laser probe of the present invention is well suited for use in treating glaucoma. In particular, as will be described in greater detail herein, the laser probe is configured to be coupled to a laser source and transmit laser energy from the laser source to the trabecular meshwork 13, resulting in photoablation of tissue (including at least the trabecular meshwork 13 and, in some instances, the Schlemm's canal 11) for the creation of channels in the meshwork (and potentially Schlemm's canal 11, thereby improving fluid drainage into the Schlemm's canal 11 and reducing intraocular pressure in the eye.

Figure 3:
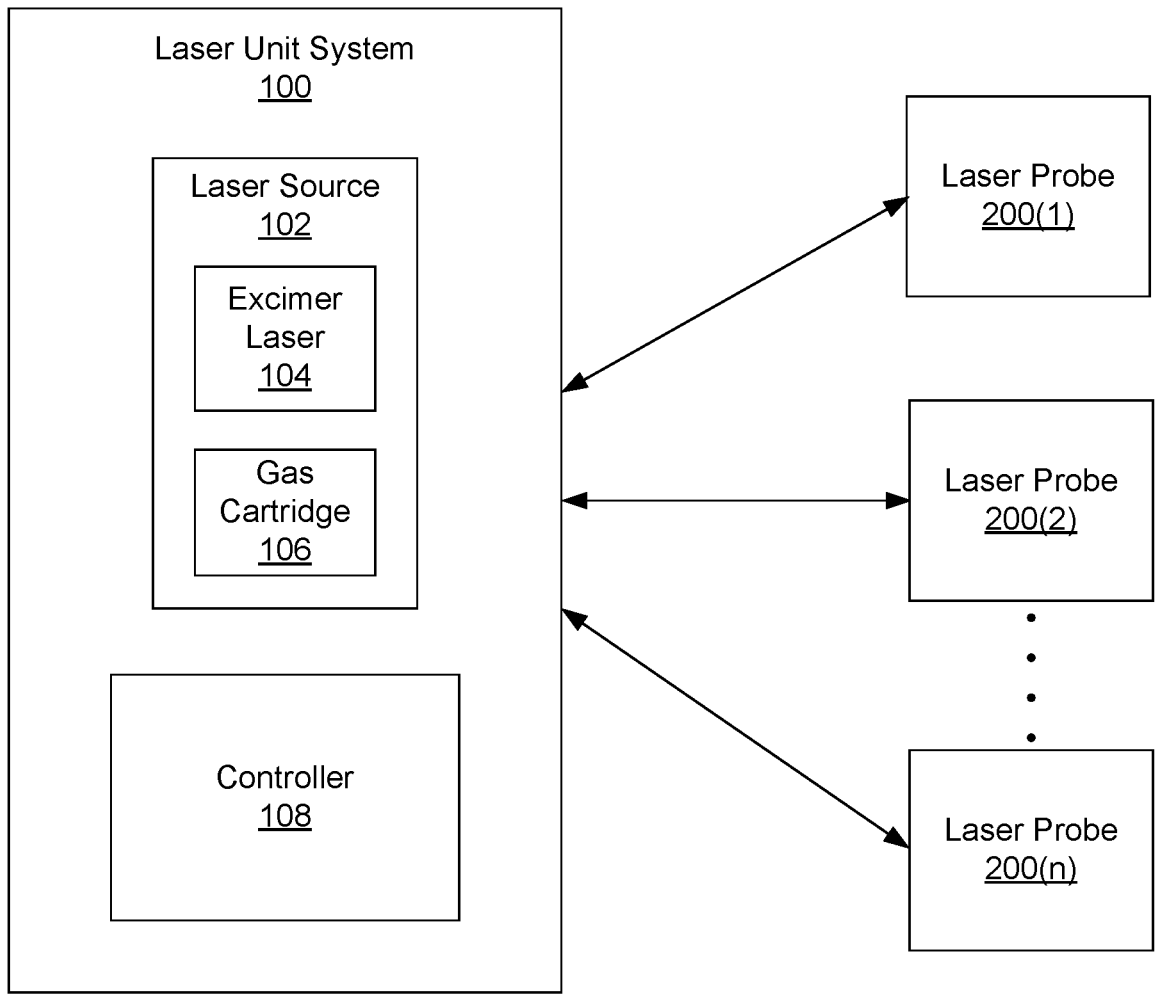
FIG. 3 diagrams an excimer laser system of the present disclosure.

FIG. 3 diagrams an excimer laser system, including a laser unit system 100 and a plurality of laser probes 200(1), 200(2), 200(n) couplable to the laser unit system 100. The system 100 includes a laser source 102 for generating laser energy and a controller 108 for controlling output of the laser energy. The laser source 102 includes an excimer laser 104 and a gas cartridge 106 for providing the appropriate gas combination to the laser 104. The excimer laser 104 is a form of ultraviolet laser that generally operates in the UV spectral region and generates nanosecond pulses. The excimer gain medium (i.e., the medium contained within the gas cartridge 106) is generally a gas mixture containing a noble gas (e.g., argon, krypton, or xenon) and a reactive gas (e.g., fluorine or chlorine). Under the appropriate conditions of electrical stimulation and high pressure, a pseudo-molecule called an excimer (or in the case of noble gas halides, exciplex) is created, which can only exist in an energized state and can give rise to laser light in the UV range.

Laser action in an excimer molecule occurs because it has a bound (associative) excited state, but a repulsive (dissociative) ground state. Noble gases such as xenon and krypton are highly inert and do not usually form chemical compounds. However, when in an excited state (induced by electrical discharge or high-energy electron beams), they can form temporarily bound molecules with themselves (excimer) or with halogens (exciplex) such as fluorine and chlorine. The excited compound can release its excess energy by undergoing spontaneous or stimulated emission, resulting in a strongly repulsive ground state molecule which very quickly (on the order of a picosecond) dissociates back into two unbound atoms. This forms a population inversion. The excimer laser 104 of the present system 100 is an XeCl excimer laser and emits a wavelength of 308 nm.

As will be described in greater detail herein, many of the components of the laser unit system 100 may be contained in a housing, such as a moveable platform, to be provided in a setting in which the procedure is to be performed (e.g., operating room, procedure room, outpatient office setting, etc.) and the probes 200(1)-200(n) may connect to the housing for use during treatment. Upon coupling a probe 200 to the housing, a fiber optic core of the probe 200 is coupled to the laser source 102 and adapted to direct laser radiation from the laser source 102, through the fiber, and to the treatment area.

The controller 108 provides an operator (i.e., surgeon or other medical professional) with control over the output of laser signals (from the excimer laser 104 to a fiber optic core of the probe 200) and, in turn, control over the transmission of laser energy from probe 200. The controller 108 may include software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. For example, the controller 108 may include a hardware processor coupled to non-transitory, computer-readable memory containing instructions executable by the processor to cause the controller to carry out various functions of the laser system 100 as described herein.

Figure 4:
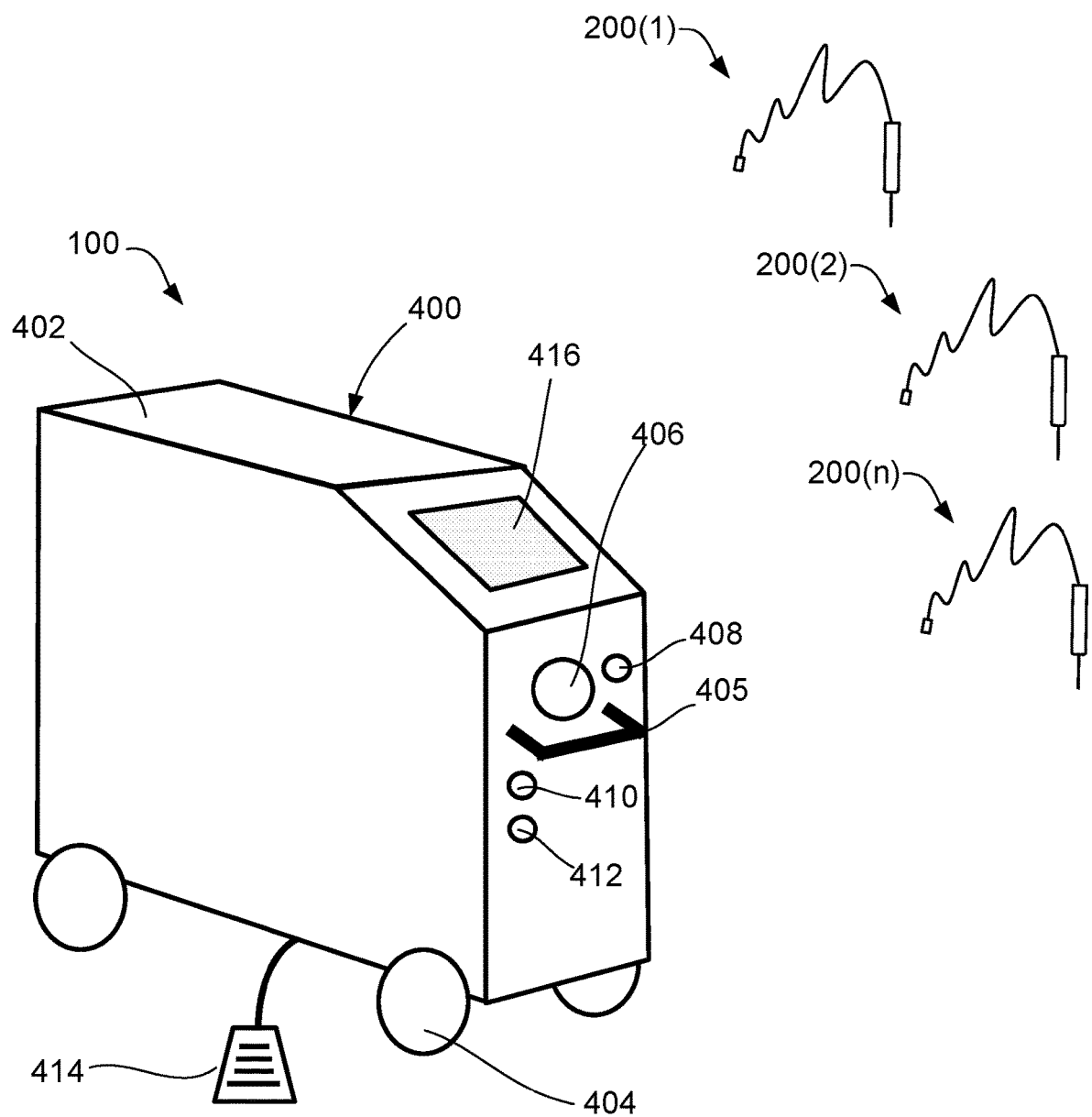
FIG. 4 shows an embodiment an excimer laser unit.

FIG. 4 shows an embodiment an excimer laser unit 100 provided in an instrument 400. As previously described, one or more components of the system 100 can be contained within the instrument 400. In the present embodiment, the laser source 102 (including the excimer laser 104 and gas cartridge 106) and controller 108 are contained within a housing 402. The housing 402 has wheels 404 and is portable. The instrument 400 further includes a push-pull handle 405 which assists with portability of the instrument 400. The instrument 400 further includes a connection port 406 for receiving a connecting end of the laser probe 200 to establish a connection between a fiber optic core of the probe 200 and the laser source 102. The instrument 400 further includes various inputs for the operator, such as an emergency stop button 410, and a power switch 412. The instrument 400 further includes a foot pedal 414 extending from the housing 402 and is operable to provide control over the delivery of shots from the excimer laser 104 to the fiber optic core of the probe 200. The instrument 400 further includes a display 416, which may be in the form of an interactive user interface. In some examples, the interactive user interface displays patient information, machine settings, and procedure information. As previously described, an operator may manually input the laser probe data via the interactive user interface to thereby provide such data to the controller 108. However, in some embodiments, the data may be automatically read from a readable device or label on the probe 200 via an associated reader of the system 100.

As shown, the present invention provides for a plurality of personalized laser probes 200(1)-200(n) for use with the excimer laser unit 100. The laser probes 200(1)-200(n) are single-use, disposable probes configured for use with a laser unit, one at a time. Upon coupling a laser probe 200 to the laser unit (via the connection portion 406, the fiber optic core of the probe 200 is adapted to direct laser radiation from the excimer laser 104 to a delivery tip of the probe for transmitting laser energy to a desired treatment area. As will be described in greater detail herein, each laser probe 200(1)-200(n) may include one or more characteristics tailored to a given user (e.g., a surgeon or other medical professional to perform a procedure involving laser treatment). As such, only single excimer laser unit 100 is required and a plurality of differently configured probes 200(1)-200(n) can be used with the unit 100.

Figure 5:
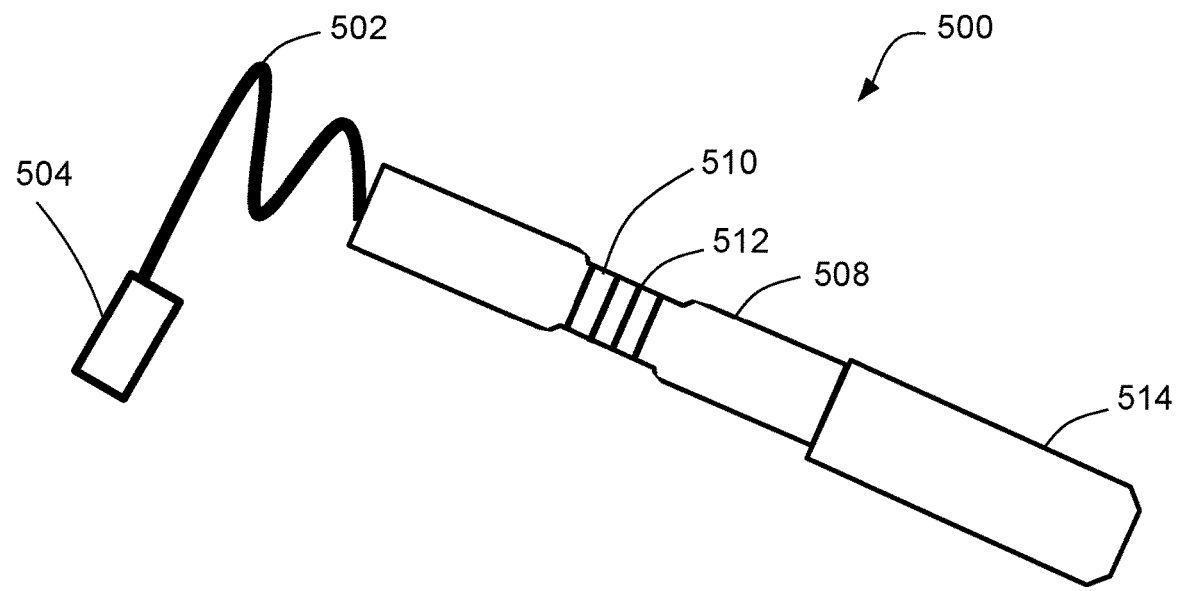
FIG. 5 shows an embodiment of a probe for use with the excimer laser system.
Figure 6:
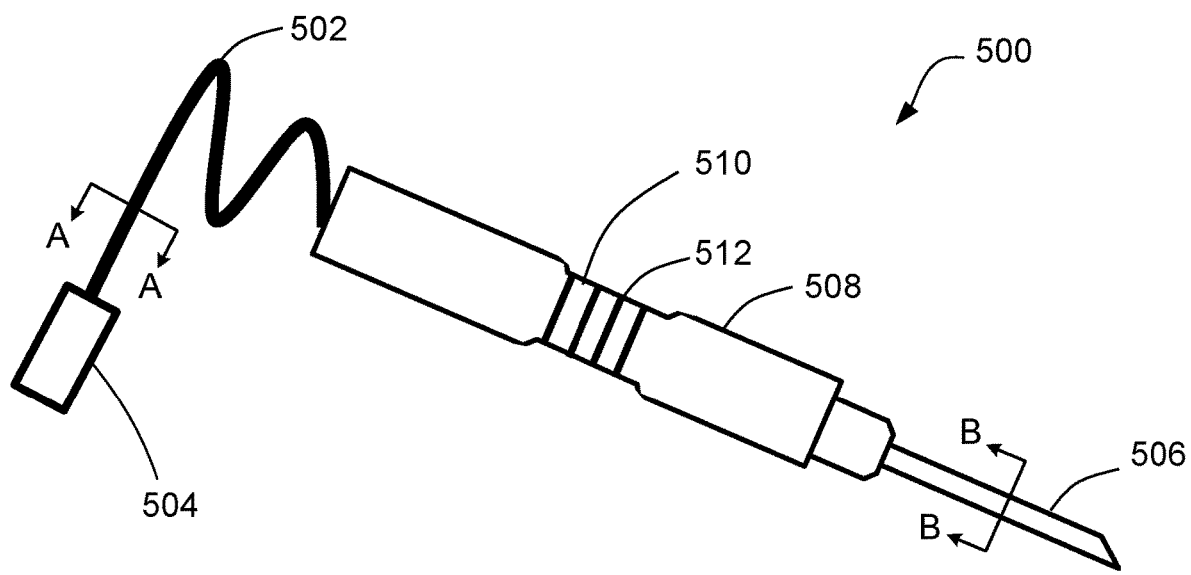
FIG. 6 shows an embodiment of a probe for use with the excimer laser system.

FIG. 5 shows an embodiment of a probe 500 for use with the excimer laser system 100, illustrating the probe 500 having a capped, distal delivery tip 506. FIG. 6 shows an embodiment of the probe 500 with the cap 514 removed, exposing the delivery tip 506 of the probe 500. The probe 500 is a single use, disposable unit. The probe 500 generally includes a fiber core coupled to the laser source 102 by way of a connector 502 (elongated cord) extending from the body of the probe 500 and having a connection assembly 504 configured to be received within the connection port 406 of the instrument 400. The probe 500 further includes a delivery tip 506 from which laser energy (from the fiber core) may be emitted. The probe 500 includes a handheld body 508, which may include a finger grip 510 with ridges or depressions 512. The body 508 of the handheld probe 500 may be metal or plastic.

FIGS. 7 and 8 show cross-sectional views of the probe 500 taken along line A-A and line B-B of FIG. 6, respectively. As shown, a fiber optic core 518 runs through the probe 500 and forms part of the connector 502. A protective sheath 516 surrounds the fiber optic core 518. In some examples, the protective sheath 516 is a protective plastic or rubber sheath. The fiber optic core 518 further form part of the delivery tip 506 of the probe 500. A metal jacket 520 surrounds the fiber optic core 518 and optical fiber 520. In some instances, a stainless steel jacket 520 surrounds and protects the fiber optic core 518.

Each laser probe includes one or more characteristics tailored to a given user (e.g., a surgeon or other medical professional to perform a procedure involving laser treatment). The specific characteristics of any given probe are based on individual preferences of a given user. The characteristics may generally relate to shape and/or dimensions of portions of the probe as well as physical qualities of portions of the probe. In some embodiments, the handheld body 508 of a given probe may include specific dimensions, including width, length, and diameter, based on individual preferences of a surgeon to improve fit and feel.

Figure 11:
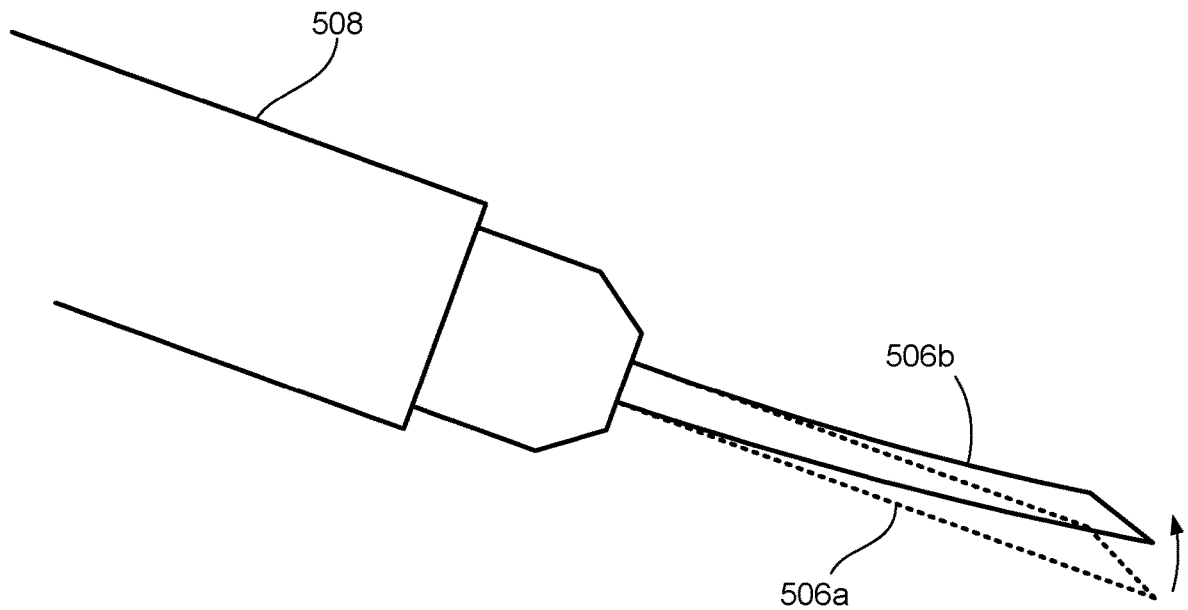
FIGS. 11 and 12 show enlarged views of a distal portion of a probe flexing in different directions.
Figure 12:
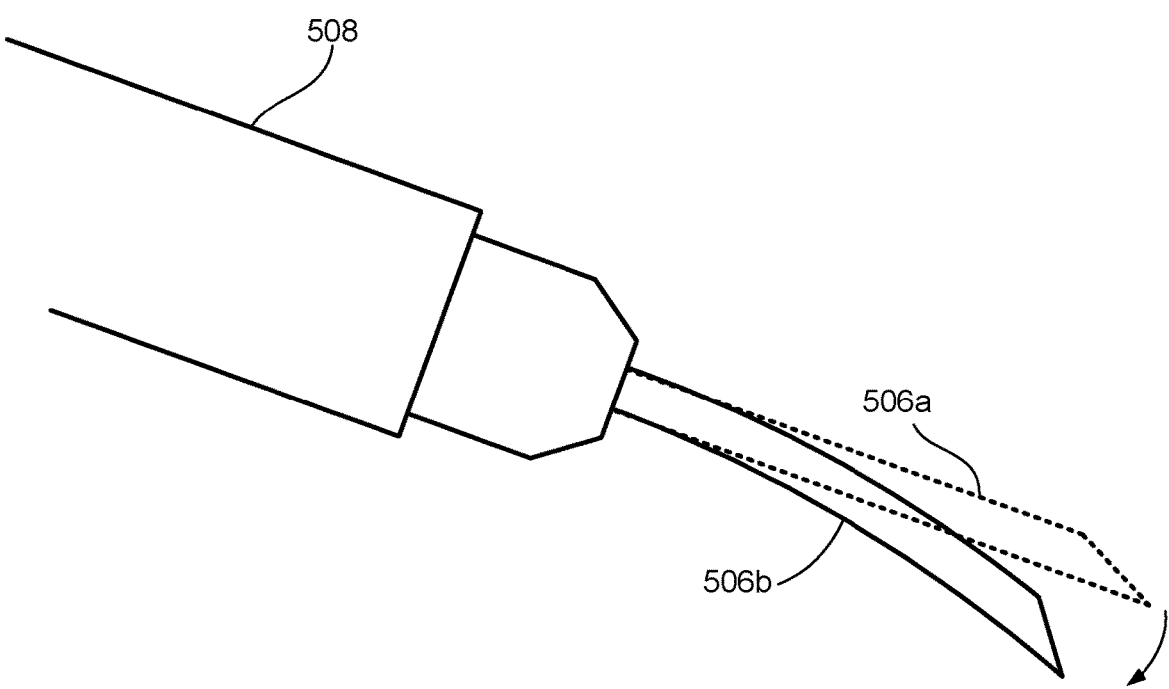

In some embodiments, the profile of the delivery tip 506 of the fiber optic core may be shaped based on preferences of a surgeon, wherein the tip may be beveled at a desired angle to enable more precise control over the procedure. FIG. 9 shows an enlarged view of a distal portion of a probe. FIGS. 10A and 10B show enlarged views of delivery tips 506 of a probe having different bevel angles 507. For example, as shown in FIG. 10A, the bevel angle $\theta_1$ may be greater than the bevel angle $\theta_1$, as determined by a user's individual preferences. Additionally, or alternatively, the distal end of the laser probe may have a specific degree of flexibility or rigidity based on based on preferences of a surgeon, further providing improved feel and maneuverability over the procedure. For example, FIGS. 11 and 12 show enlarged views of a distal portion 506a of a probe flexing in different directions (flexed distal portion 506b). As such, the outer jacket 520 surrounding said fiber optic core 518 may include certain materials having properties allowing for desired flex or rigidity.

The personalization of laser probes provides surgeons with tailored fit, feel, and function. Surgeons are better equipped to successfully perform a given procedure that may otherwise prove difficult due to the lack of variation among laser fiber options. In particular, the laser probes and laser unit of the present invention are preferably used for permanent treatment of glaucoma using laser trabeculostomy. For example, during a laser trabeculostomy procedure using the laser system and probes of the invention, a physician guides the delivery tip of the probe through a corneal incision in the eye and towards the trabecular meshwork. A Gonio lens and/or illumination source may be used by the physician to aid in positioning the delivery tip. In some examples, the physician uses a light source, such as Gonio lens, endoscope, or other illumination source, to aid in adjusting placement of the probe.

By providing personalized laser probes, a surgeon is more comfortable with the laser probe and able to perform the procedure with the required precision to ensure optimal laser treatment of the target area. For example, the surgeon is able to better position laser emission transverse to the Schlemm's canal. Once the delivery tip is at a position transverse to the Schlemm's canal, the physician delivers a series of shots of laser energy to the trabecular meshwork. By providing a laser probe at a position transverse to the Schlemm's canal, or crosswise to the Schlemm's canal, the laser is delivered to a greater amount of surface area than if the laser was in a parallel or perpendicular position to the Schlemm's canal. Thus, arrangement of the delivery tip at a position transverse to the Schlemm's canal achieves optimal photoablation and channel formation in the meshwork and/or Schlemm's canal. The orientation and positioning of the delivery tip is critical when creating channel formation in the tissue, as achieving transverse placement of channels in the meshwork relative to Schlemm's canal provides optimal drainage. Arranging the laser probe at a position transverse to Schlemm's canal provides optimum results by providing a greater amount of surface area for photoablation by the laser, resulting in improved perforation and thus improved fluid drainage.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for performing intraocular procedures, said method comprising:

coupling a first laser probe to a laser unit, wherein the first laser probe is one of a plurality of single-use, disposable laser probes coupleable, one at a time, to the laser unit;

applying first laser energy to an eye of a first patient during a first intraocular procedure using the laser unit and the first laser probe;

removing the first laser probe from the laser unit;
coupling a second laser probe to the laser unit, wherein the second laser probe is one of the plurality of single-use, disposable laser probes; and
applying second laser energy to an eye of a second patient during a second intraocular procedure using the laser unit and the second laser probe,
wherein the plurality of single-use, disposable laser probes comprise:
a handheld component; and
a fiber optic core extending through the handheld component, the fiber optic core including a proximal end detachably coupleable to the laser unit and a distal end including a delivery tip for emitting laser energy, transmitted via the fiber optic core from said laser source when coupled thereto, to a target tissue for ablation thereof, wherein each of said plurality of single-use, disposable laser probes comprises one or more characteristics tailored to a respective user, such that the first laser probe has a first personalization and the second laser probe has a second personalization different from the first personalization, wherein the first personalization comprises a first delivery tip with a first flexibility level and the second personalization comprises a second delivery tip with a second flexibility level different from the first flexibility level.

2. The method of claim 1, wherein the first laser probe further has a third personalization comprising a first delivery tip with a first delivery tip bevel angle and the second laser probe further has a fourth personalization comprising a second delivery tip with a second delivery tip bevel angle different from the first delivery tip bevel angle.

3. The method of claim 1, wherein the first laser probe further has a third personalization comprising a first size of said handheld component of the first laser probe and the second laser probe further has a fourth personalization comprising a second size of said handheld component of the second laser probe different from the first size.

4. The method of claim 1, further comprising an outer jacket surrounding said fiber optic core.

5. The method of claim 4, wherein said outer jacket has a degree of rigidity or flexibility based on a preference of said respective user.

6. The method of claim 1, wherein said intraocular procedures are laser trabeculostomies.

7. The method of claim 5, wherein said target tissue comprises at least one of a trabecular meshwork and Schlemm's canal.

8. The method of claim 1, wherein the first laser probe and the second laser probe are provided such that a desired probe with a desired flexibility level is selectable by a surgeon to provide desired feel and maneuverability during the intraocular procedure.

9. The method of claim 1, further comprising:
inserting the first laser probe through a corneal incision of the eye of the first patient,
moving the first laser probe through the eye toward a trabecular meshwork of the eye of the first patient, and
placing the first delivery tip relative to the trabecular meshwork, such that upon emitting the laser energy from the first delivery tip a channel is created in the trabecular meshwork.

10. The method of claim 1, wherein the first laser probe or the second laser probe is selectable by an operator for performing a given intraocular procedure to enhance proper placement of the first or second delivery tip relative to a trabecular meshwork of the eye of the first patient or the second patient.

11. The method of claim 1, wherein the first laser probe or the second laser probe is selectable by an operator to avoid unintended collateral tissue damage or the creation of channels in a trabecular meshwork of the eye of the first patient or the second patient that are inadequate and do not provide desired drainage of aqueous humor fluid through the trabecular meshwork into a Schlemm's canal of the eye.

12. A kit for use in performing an intraocular procedure, said kit comprising:
a plurality of single-use, disposable laser probes coupleable, one at a time, to a laser unit comprising an excimer laser source, each single-use, disposable laser probe comprising:
a handheld component;
a fiber optic core extending through the handheld component, the fiber optic core including a proximal end detachably coupleable to the laser unit and a distal end including a delivery tip for emitting laser energy, transmitted via the fiber optic core from said laser source when coupled thereto, to a target tissue for ablation thereof;
wherein each of said plurality of single-use, disposable laser probes comprises one or more characteristics tailored to a respective user, such that a first probe has a first personalization and a second probe has a second personalization different from the first personalization, wherein the first personalization comprises a first delivery tip with a first flexibility level and the second personalization comprises a second delivery tip with a second flexibility level different from the first flexibility level.

13. The kit of claim 12, wherein the first laser probe further has a third personalization comprising a first size of said handheld component of the first probe and the second laser probe further has a fourth personalization comprising a second size of said handheld component of the second probe different from the first size.

14. The kit of claim 13, wherein the first size and the second size refer to a width of the first probe and the second probe.

15. The kit of claim 13, wherein the first size and the second size refer to a length of the first probe and the second probe.

16. The kit of claim 13, wherein the first size and the second size refer to a diameter of the first probe and the second probe.

17. The kit of claim 12, wherein the first laser probe further has a third personalization comprising a first delivery tip with a first delivery tip bevel angle and the second laser probe further has a fourth personalization comprising a second delivery tip with a second delivery tip bevel angle different from the first delivery tip bevel angle.

18. The kit of claim 12, wherein each single-use, disposable laser probe comprises an outer jacket surrounding said fiber optic core.

19. The kit of claim 18, wherein said outer jacket has a degree of rigidity or flexibility based on a preference of said respective user.

20. The kit of claim 12, wherein the first probe and second probe have different finger grip patterns.

21. The kit of claim 12, wherein said intraocular procedure is a laser trabeculostomy and said target tissue comprises at least one of a trabecular meshwork and Schlemm's canal.

22. A system for use in performing an intraocular procedure, said system comprising:
- a laser unit comprising a laser source; and
- a plurality of single-use, disposable laser probes coupleable, one at a time, to said laser unit, each single-use, disposable laser probe comprising:
  - a handheld component; and
  - a fiber optic core extending through the handheld component, the fiber optic core including a proximal end detachably coupleable to the laser unit and a distal end including a delivery tip for emitting laser energy, transmitted via the fiber optic core from said laser source when coupled thereto, to a target tissue for ablation thereof, wherein:
    - the first probe or the second probe is selectable by an operator of the system for performing a given intraocular procedure to provide desired maneuverability or comfort for an operator of the laser unit during the intraocular procedure; and
    - each of said plurality of single-use, disposable laser probes comprises one or more characteristics tailored to a respective user, such that a first probe has a first personalization and a second probe has a second personalization different from the first personalization, wherein the first personalization comprises a first delivery tip with a first flexibility level and the second personalization comprises a second delivery tip with a second flexibility level different from the first flexibility level.

23. The system of claim 22, wherein the first laser probe further has a third personalization comprising a first size of said handheld component of said first probe and the second laser probe further has a fourth personalization comprising a second size of said handheld component of said second probe different from the first size.

* * * * *